(12) United States Patent
North

(10) Patent No.: US 9,655,784 B2
(45) Date of Patent: May 23, 2017

(54) COLD WEATHER WELDING MASK HAVING HEATED FORCED AIR MEANS

(71) Applicant: Kelvin North, Medicine Hat (CA)

(72) Inventor: Kelvin North, Medicine Hat (CA)

( * ) Notice: Subject to any disclaimer, the term of this patent is extended or adjusted under 35 U.S.C. 154(b) by 709 days.

(21) Appl. No.: 13/870,563

(22) Filed: Apr. 25, 2013

(65) Prior Publication Data

US 2013/0312151 A1 Nov. 28, 2013

Related U.S. Application Data

(60) Provisional application No. 61/650,788, filed on May 23, 2012.

(51) Int. Cl.
*A61F 9/06* (2006.01)

(52) U.S. Cl.
CPC ..................... *A61F 9/06* (2013.01)

(58) Field of Classification Search
CPC .. A61F 9/06; A61F 9/061; A61F 9/064; A61F 9/068; A42B 3/225; A42B 3/24; A42B 3/245; A42B 3/28; A42B 3/281; A42B 3/283; A42B 3/285; A42B 3/286
USPC ..................... 2/435, 437, 439, 9, 7
See application file for complete search history.

(56) References Cited

U.S. PATENT DOCUMENTS

| | | | | |
|---|---|---|---|---|
| 3,096,430 A * | 7/1963 | Farr | ........................ | A61F 9/061 2/8.3 |
| 3,238,535 A * | 3/1966 | Richey | ...................... | A61F 9/06 2/8.1 |
| 3,467,965 A * | 9/1969 | Murphy | .................. | A61F 9/068 128/201.25 |
| 3,548,415 A * | 12/1970 | Waters | .................... | A42B 3/286 165/46 |
| 3,657,740 A * | 4/1972 | Cialone | ................... | A61F 9/068 128/205.25 |
| 3,825,953 A * | 7/1974 | Hunter | ..................... | A61F 9/028 2/437 |
| 3,943,573 A * | 3/1976 | Budmiger | ................. | A61F 9/06 2/432 |
| 4,150,443 A * | 4/1979 | McNeilly | ................ | A61F 9/028 2/171.3 |
| 4,155,122 A * | 5/1979 | Budmiger | ............... | A61F 9/065 2/8.7 |
| 4,293,757 A | 10/1981 | Niemi | | |

(Continued)

*Primary Examiner* — Alissa L Hoey
(74) *Attorney, Agent, or Firm* — Global Intellectual Property Agency, LLC

(57) ABSTRACT

A cold climate welding mask is provided for combatting interior fogging, condensation, and frost development within the welding mask interior. The device comprises a welding mask structure, a forced air means, a heating means, and a power supply for injecting a heated air stream through the mask interior to remove the user's breath therefrom and to warm the mask interior for comfort purposes. Also provided is a welding mask lens having internal heating elements therein for direct fog prevention. The device may comprises an attachable, auxiliary unit that is attachable to a traditional welding mask, or preferably the device comprises a defined welding mask structure having the elements embedded therein for cold climate and cold environmental welding use. Ideally the device is provided for use by welding operators working in extremely cold or outdoor climates where a user's breath can create internal fogging, condensation, and frost within the mask interior.

13 Claims, 5 Drawing Sheets

(56) References Cited

U.S. PATENT DOCUMENTS

| | | | |
|---|---|---|---|
| 4,309,774 A * | 1/1982 | Guzowski | A61F 9/068 2/171.3 |
| 4,443,893 A * | 4/1984 | Yamamoto | A61F 9/028 2/171.3 |
| 4,498,202 A * | 2/1985 | Yamamoto | A42B 3/24 2/171.3 |
| 4,546,496 A * | 10/1985 | Lewis | A42C 5/04 2/171.3 |
| 4,682,007 A * | 7/1987 | Hollander | A42B 3/245 2/435 |
| 4,744,106 A * | 5/1988 | Wang | A42B 3/286 2/171.3 |
| 4,890,335 A * | 1/1990 | Crowson | A61F 9/068 2/171.3 |
| 5,031,237 A * | 7/1991 | Honrud | A61F 9/068 128/201.25 |
| 5,054,480 A | 10/1991 | Bare et al. | |
| 5,104,430 A * | 4/1992 | Her-Mou | A62B 18/006 128/205.29 |
| 5,123,114 A | 6/1992 | Desanti | |
| 5,555,879 A * | 9/1996 | Helin | A61F 9/068 128/200.28 |
| 5,561,855 A * | 10/1996 | McFall | A61F 9/068 2/171.3 |
| 5,878,742 A * | 3/1999 | Figueredo | A62B 18/003 128/201.24 |
| 5,896,579 A | 4/1999 | Johnson et al. | |
| 6,032,291 A * | 3/2000 | Asenguah | A42B 1/008 2/171.3 |
| 7,178,932 B1 | 2/2007 | Buckman | |
| 7,534,005 B1 | 5/2009 | Buckman | |
| 8,807,814 B1 * | 8/2014 | Glenn | F21V 33/0096 2/171.3 |
| 2007/0113324 A1 * | 5/2007 | Chen | A42B 3/044 2/424 |
| 2008/0141442 A1 * | 6/2008 | Chen | A42B 3/286 2/411 |
| 2009/0025125 A1 * | 1/2009 | Jou | B63C 11/12 2/428 |
| 2009/0235438 A1 * | 9/2009 | DiPaola | A42B 3/245 2/435 |
| 2009/0276940 A1 * | 11/2009 | Sallee | A42B 3/24 2/435 |
| 2010/0299795 A1 * | 12/2010 | Uttrachi | F16P 1/06 2/8.6 |
| 2011/0126345 A1 * | 6/2011 | Matsumoto | A61F 9/028 2/435 |
| 2011/0231977 A1 * | 9/2011 | Rupnick | A42B 3/286 2/7 |
| 2011/0285957 A1 * | 11/2011 | Mikulenka | A61F 9/028 351/62 |
| 2012/0167282 A1 * | 7/2012 | Fleming | A42B 3/286 2/410 |
| 2012/0246808 A1 * | 10/2012 | Spiro | A42B 3/24 2/424 |
| 2014/0143934 A1 * | 5/2014 | Grzybowski | A42B 3/286 2/171.3 |

* cited by examiner

COLD WEATHER WELDING MASK HAVING HEATED FORCED AIR MEANS

CROSS REFERENCE TO RELATED APPLICATION

This application claims the benefit of U.S. Provisional Application No. 61/650,788 filed on May 23, 2012, entitled "Welding Hood Defroster." The above identified patent application is herein incorporated by reference in its entirety to provide continuity of disclosure.

BACKGROUND OF THE INVENTION

Field of the Invention

The present invention relates to welding masks and utility shields. More specifically, the present invention pertains to a cold weather welding mask that prevents humidity from building up as condensation on the welding lens as a user's expelled breath turns into condensation that readily fogs over the lens. The device includes a heated, forced air means and lens heating element to maintain vision through the lens when utilized in cold climates.

Welding operations involve a joining process of metal or thermoplastic material, wherein the two materials are melted together in conjunction with a filler material to create a permanent bond therebetween. The welding process involves a high energy sources that expel tremendous levels of light and heat that can be hazardous to be in proximity to without proper safeguards. Generally the welding process is conducted using a hand tool to establish the welding bond line and to control the application of heat and filler material being inserted into the joint. This requires skill and experience to master, but also requires a worker to be very close to the work piece and thus the high energy source.

To protect the welder, the user is generally adorned in heavy, non-flammable garments, welding gloves to protect his or her hands, and finally a welding mask to shield the user's face from the products of the welding process. The brightness and intensity of the welding process can cause severe injuries to the user's eyes and even burning of the user's face. Open exposure to the brightness can lead to inflammation of the cornea and even burns to the retina. Therefore, most welding masks are full-face and include a darkened lens that allows the welder to visualize the joint and the welding process while the arc is visible. The lens is darkened to reduce the transmission to the user's eyes, therefore reducing any damage thereto from direct viewing. A final concern for welders is the exposure of the welder to the noxious gases and particulate matter from the welding process. Various oxides in the fumes and those containing heavy metals from the welding process can be hazardous if inhaled, particularly over the long term. Therefore the welding process is conducted in a ventilated area if possible, however this is not always possible and therefore exposure is inevitable in some cases.

While most available welding masks provide a means of shielding the user's face and eyes from the welding flame, they provide little in the way of ventilation or condensation removal. Operating in colder climates and in outdoor environments, in particular, where the air can be below freezing, can lead to condensation build-up within the mask, fogging of the mask lens, and frosting of the interior of the mask while in use. Some available welding masks provide a means of ventilating the interior of a mask; however these are largely ineffective in very cold climates for those welders operating outdoors on pipelines and the like.

The present invention provides a new and novel welding mask that includes a forced air means and a heating means that directs heated air into the interior of the welding mask. This elevates the temperature within the mask for user comfort and also prevents fogging of the welding mask caused by the user's breath and built-up condensation. To further facilitate this, the welding lens itself may further incorporate a plurality of resistive heating elements therein to directly heat the lens for combatting lens fogging. Overall the device comprises a unitary welding mask having the attached elements, or alternatively the heating means and forced air means may be clipped onto an existing, conventional welding mask to update its general use for that of colder, outdoor climates.

Description of the Prior Art

Devices have been disclosed in the prior art that relate to welding masks and those that include forced are means. These include devices that have been patented and published in patent application publications, and generally relate to welding masks that utilize exterior air and a forced air means to circulate air for ventilation purposes. None of the devices contemplates a heating element that would make the mask suitable for cold, outdoor welding climates where a user's breath can create condensation, lens fogging, and interior ice buildup. The following is a list of devices deemed most relevant to the present disclosure, which are herein described for the purposes of highlighting and differentiating the unique aspects of the present invention, and further highlighting the drawbacks existing in the prior art.

Specifically, U.S. Pat. Nos. 7,178,932 and 7,534,005 to Buckman disclose a self-contained welding helmet that improves ventilation of air through the helmet to protect the welder from noxious fumes during a welding process and for reducing lens condensation. The helmet includes an electrically driven fan along the front wall of the helmet that draws air through air inlet port and an air filter. The filtered air is then directed upward against the helmet lens to reduce condensation and downwards to vent air out of the helmet. The fan is driven by a power source that can be charged by a photovoltaic element along the upper portion of the helmet. The Buckman devices, while providing a ventilated welding mask, fails to disclose a heating means such that the mask would be appropriate for welding use in extremely cold climates.

Another such device is U.S. Pat. No. 5,123,114 to Desanti, which discloses a ventilated welding mask having an exterior housing for drawing in and directing an air flow through a conduit and thereafter through a metering manifold within the mask interior. The manifold allows the user to control the flow air entering the mask by blocking the flow therethrough. A second medical chamber within the exterior housing may further comprise a carbon dioxide cooling medium for sending a stream of cooled air onto the interior surface of the welding mask for cooling and comfort of the user. Similar to the Buckman devices, the Desanti device fails to contemplate a heating means.

U.S. Pat. No. 5,896,579 to Johnson is another such device that discloses a welding helmet with an air circulating cooling system that utilizes evaporative cooling and a fan to move clean, cooled air into the helmet interior during welding operation. A moistened evaporative cooling pad is dampened by a cooling water storage bottle by way of a moistened wick, which is utilized in conjunction with an electric fan to cool the user while welding. While evaporative cooling is useful for cooling a welder, this is not required nor desired in colder climates. The goal of the present invention is to provide a moisture reducing mask interior environment, and one that is warmed when compared to the exterior air for both comfort and for maintaining vision though the welding mask lens.

Other work mask devices that include a ventilation means include U.S. Pat. No. 4,293,757 to Niemi and U.S. Pat. No. 5,054,480 to Bare. The Niemi device describes a welding helmet with a pneumatically controlled dark eye lens and a helmet ventilation means for communicating a fresh supply of air into the helmet interior. The Bare device describes pneumatic system for a welding mask. While this is very useful for operatively protecting the user's eyes and ventilating the mask interior, the system of the Bare device is outside of the scope of that desired by the present invention, while the purpose of the Bare device is diverging in concept.

The present invention pertains to cold climate welding mask for those that engage in welding processes in extremely cold climates and in outdoor spaces. These environments cause a user's breath to condense and to fog the interior of the mask lens, and further to crystallize along the interior of the mask. Neither of these is desired. Finally, user comfort is accounted for, wherein a heating means not only reduces condensation, but also warms the user while in the harshly cold environment. It is submitted that the present invention substantially diverges in design elements from the prior art, and consequently it is clear that there is a need in the art for an improvement to existing cold climate welding mask devices. In this regard the instant invention substantially fulfills these needs.

SUMMARY OF THE INVENTION

In view of the foregoing disadvantages inherent in the known types of welding mask devices now present in the prior art, the present invention provides a new cold climate welding mask device that can be utilized for providing convenience for welders when engaging in welding process in cold climate and in outdoor spaces.

It is therefore an object of the present invention to provide a new and improved cold climate welding mask device that has all of the advantages of the prior art and none of the disadvantages.

It is another object of the present invention to provide a cold climate welding mask device that is well suited for cold environments and outdoor climates that would otherwise result in fog, condensation, and frost development within the interior of a conventional welding mask assembly if used therein.

Another object of the present invention is to provide a cold climate welding mask device that includes a forced air means and a heating means to move air through the mask interior and to heat the interior of the mask, both for comfort and to combat condensation, fogging, and frost therein.

Yet another object of the present invention is to provide a cold climate welding mask device that further includes a welding lens that has heating elements therein to directly combat fogging and to ensure clarity of vision therethrough.

Another object of the present invention is to provide a cold climate welding mask device that comprises a removable heating and forced air unit that is attachable to an existing and traditional welding mask.

Another object of the present invention is to provide a cold climate welding mask device that comprises a specifically designed welding masks structure having an embedded forced air means, heating means, and a lens heating element for ready deployment in cold environments.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
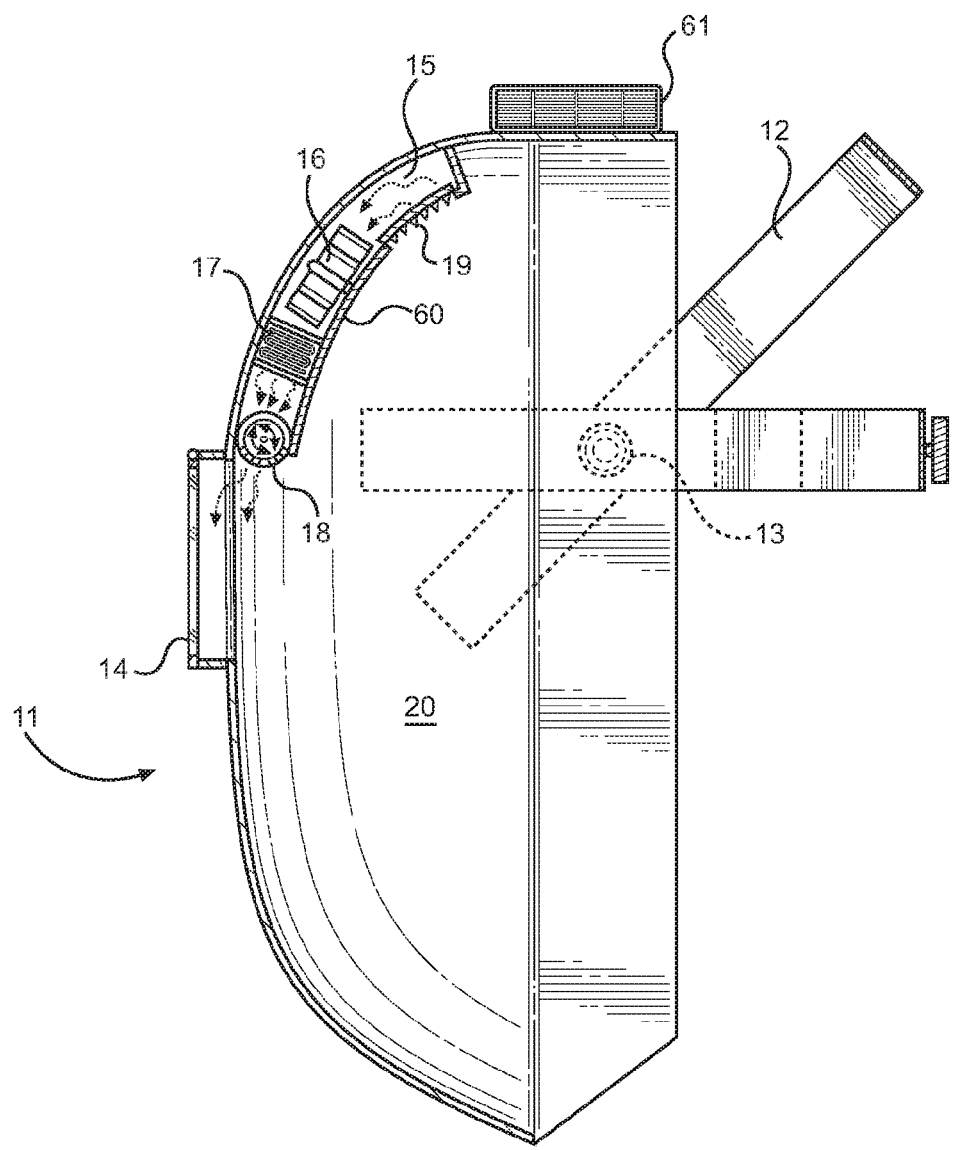
FIG. 1 shows a side view cross section of an exemplary embodiment of the present invention.

Reference is made herein to the attached drawings. Like reference numerals are used throughout the drawings to depict like or similar elements of the cold climate, anti-fog and anti-frost welding mask. For the purposes of presenting a brief and clear description of the present invention, the preferred embodiment will be discussed as used for warming the interior of a welding mask and maintain a constant air flow therethrough, wherein condensation is removed, fogging is prevented, and the interior environment of the mask is comfortably warm despite being utilized in cold weather extremes. The figures are intended for representative purposes only and should not be considered to be limiting in any respect.

Referring now to FIG. 1, there is shown a cross section side view of an exemplary embodiment of the cold climate welding mask of the present invention. The present invention provides a welding mask 11 that is ideal for use in cold weather and outdoor conditions, wherein the cold temperature would otherwise cause a user's breath to turn to condensate along the interior 20 of the welding mask 11. In extreme colds, this condensate can form frost along the mask interior 20, while the variation in temperature and moisture in the user's breath can readily fog the lens 14 of the mask and obscure vision therethrough. The present invention provides a welding mask 11 having a forced air means 16 and a heating means 17 to circulate heated air through the mask to combat these cold climate effects on the mask interior 20. The warm air functions to reduce condensation from breath, eliminate frost, reduce or eliminate fogging of the lens, and further provide an interior mask environment that is pleasant and warming to the user, which is particularly welcomed when in use outdoors in and in the extreme cold.

In an exemplary embodiment of the present invention, the mask includes a built-in air flow and heating means assembly that does not restrict, limit, or change the mask's primary function of providing protection for the user and an eye shield against the light of the welding operation. The first goal is protection, followed by improvement of the mask interior environment in cold air, while finally air is circulated to remove noxious fumes from the mask interior as a result of the welding process.

The exemplary embodiment of the mask 11 includes a mask having an outer surface adapted to shield the user's face, a hinged welding lens 14, a pivoting 13 head band 12 for attachment to a user's head, and an air heating and circulation housing 60 along the mask interior 20. The housing 60 is preferably in proximity to the welding lens 14, whereby the housing 60 provides an interior cavity and sheltered electrical assemblies for drawing in air, heating air, and exhausting the air within the mask interior and optionally directly onto the mask lens 14 for anti-fogging. The housing 60 components comprise a forced air means 16, which is preferably an electric, high efficiency fan that draws air 15 through an intake 19 within the mask interior and along the housing wall. The air 15 is then forced into a heating means 17, which is preferably a resistance heating element that rapidly heats air 15 passing over its heating elements. Finally, the housing 60 provides an exhaust port that is metered and directable by way of a vent 18, whereby the heated air can be directed as desired by the user (i.e. against the lens, against the mask interior surfaces, or against the user's face). The vent 18 is a commonly deployed shutter vent that includes hand controls, similar to those vents found in vehicle interiors for directing climate controlled air.

Figure 2:
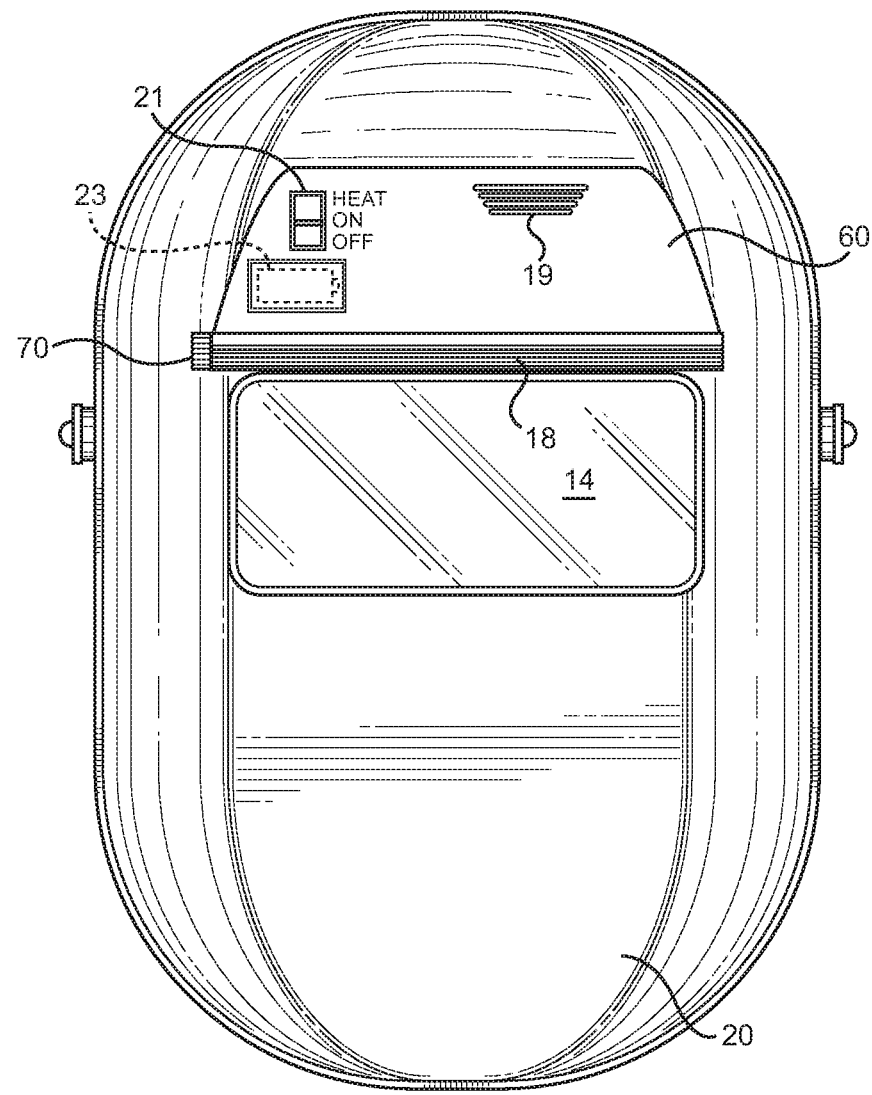
FIG. 2 shows a rear view of the exemplary embodiment, wherein the mask internal cavity is shown and the heating and forced air component housing.

The interior housing 60 therefore acts as a conduit that draws in air through an intake 19, heats and pressurizes the air, and exhausts the air through an exhaust port 18. The intake 19 may also include an air filter to remove contaminates, smells, and noxious fumes. Referring to FIG. 2, the interior 20 of the mask is visualized, wherein the housing 60 is positioned above the welding lens 14 and above the user's forehead when donned. The housing 60 includes the intake vent 19 and the controllable exhaust port 18 with hand controls 70 for controlling direction of the vent. During operation, the user can initiate the operation of the forced air means and heating means by way of a switch 21. The switch 21 allows for the device to operate with just the forced air means on or with both the forced air means and heating means on in conjunction. Therefore, the device also provides a pure circulation feature in which the forced air means circulates air without heating it. The electrical elements of the device are preferably driven by way of an internal power supply 23, such as a battery pack mounted within the housing 60 or mounted along the mask head band or along the wearer's body (e.g. a belt-supported battery pack). An alternate embodiment of the battery pack includes a photovoltaic cell 61 mounted along the upper portion of the helmet or on the external battery pack.

Figure 3:
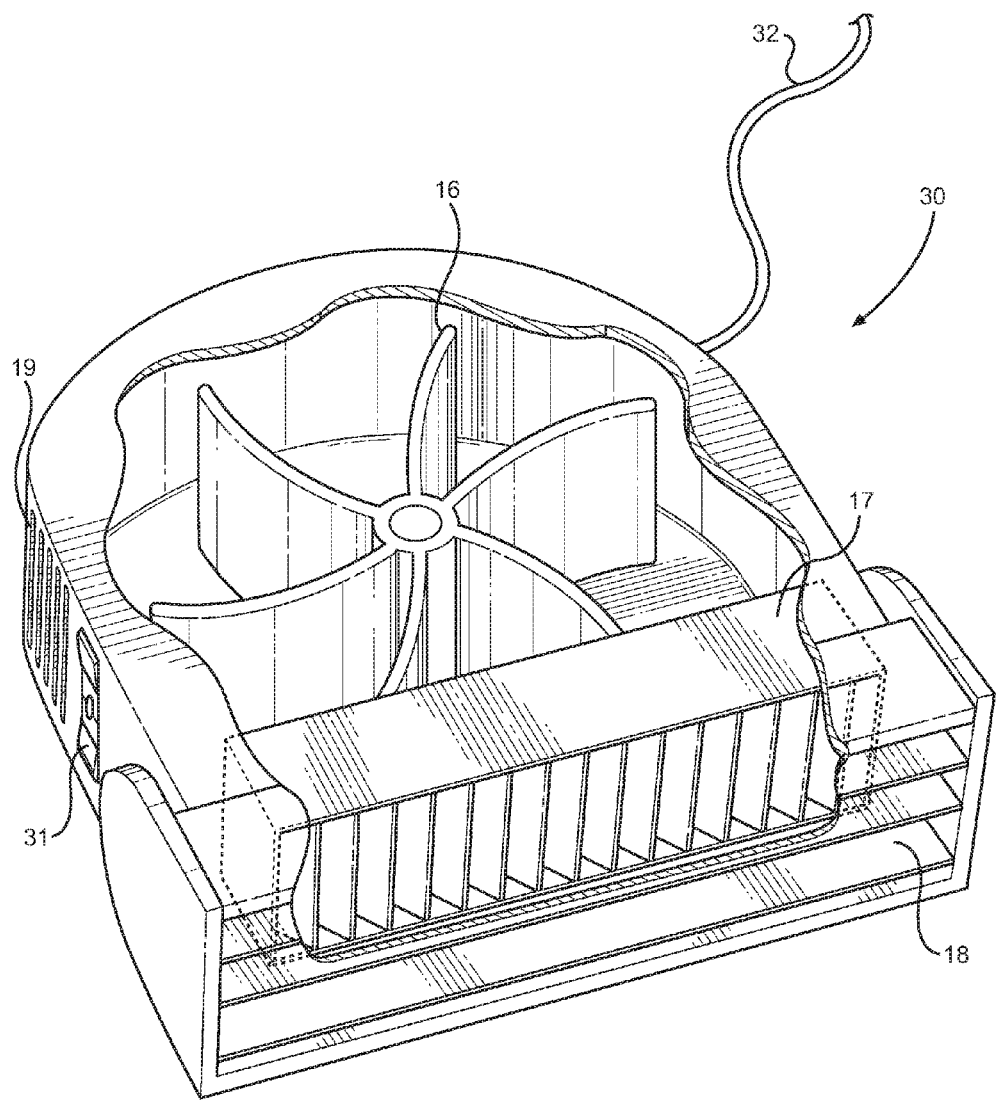
FIG. 3 shows a view of the embodiment of the present invention wherein a removable heated, forced air means is deployed within a standard welding mask.

Referring now to FIG. 3, there is shown an alternate embodiment of the present invention, wherein a removable heating and forced air assembly 30 is provided for use in conjunction with a welding mask in colder climates. The device 30 comprises an accessory that is attachable to the mask interior by way of mechanical or removable (hook and loop) fasteners, whereby the device circulates air and heats the air on command to provide the same benefits as the exemplary embodiment of the present invention, yet in a condensed and more flexibly-deployed structure that can function with existing welding mask structures.

The device 30 comprises a handheld housing assembly that includes an interior cavity, a vented intake port 19, and a vented exhaust port 18. Within the interior is forced air means, such as a circulating fan 16 that draws air through the intake 19 and forces it through a heating means 17 just before exiting the interior through the exhaust port 18 and into the welding mask interior space. The heating means 17 is preferably an electrically resistive heating element that rapidly heats the air as it passes over its structure. The heating elements are positioned within an air pathway such that it heats air passing over the elements, similar to a heat exchanger. The heated air is forced therethrough and out of the exhaust vent 18, which is ideally positioned in proximity to the welding mask lens to defog the same and to spread warm air into the mask to combat condensation and frost.

Figure 4:
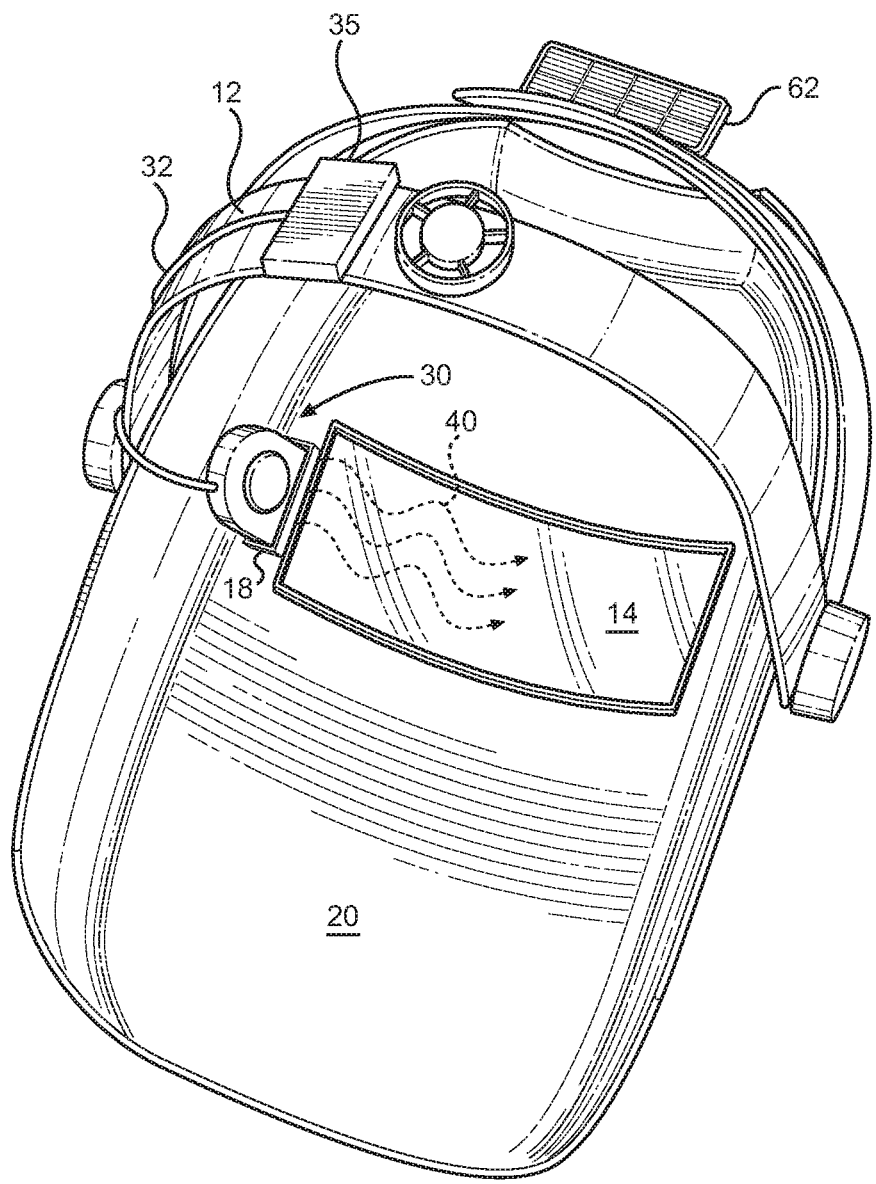
FIG. 4 shows a view of the removable embodiment of the present invention installed within a standard welding mask interior.

The assembly is a module or accessory that is applied to the interior of a conventional welding mask to heat the interior thereof. Referring to FIGS. 3 and 4, the assembly includes a power switch 31 to operate the electrical fan 16 independently or in conjunction with the heating element 17. The switch 31 controls the operation of the device, whereby electrical power is drawn through a cord 32 that attaches to a power supply 35 mounted along the mask interior 20 or along the headband 12 thereof. The power supply 35 can further be mounted along the user's person rather than along the mask headband. As with the first embodiment of the present invention, the external battery pack 35 can further be assisted or charged by a photovoltaic cell 62 there attached. The power supply 35 supplies electrical power to the assembly for continued operation, wherein the supply can be replenished and replaced as necessary. An alternate embodiment contemplates a power supply attached to the housing of the assembly 30. Therefore, the assembly 30 operates independently of outside electrical connections outside the mask, whereby forced and/or heated air 40 is directed against the mask interior 20 or against the mask lens 14 in cold climates.

Figure 5:
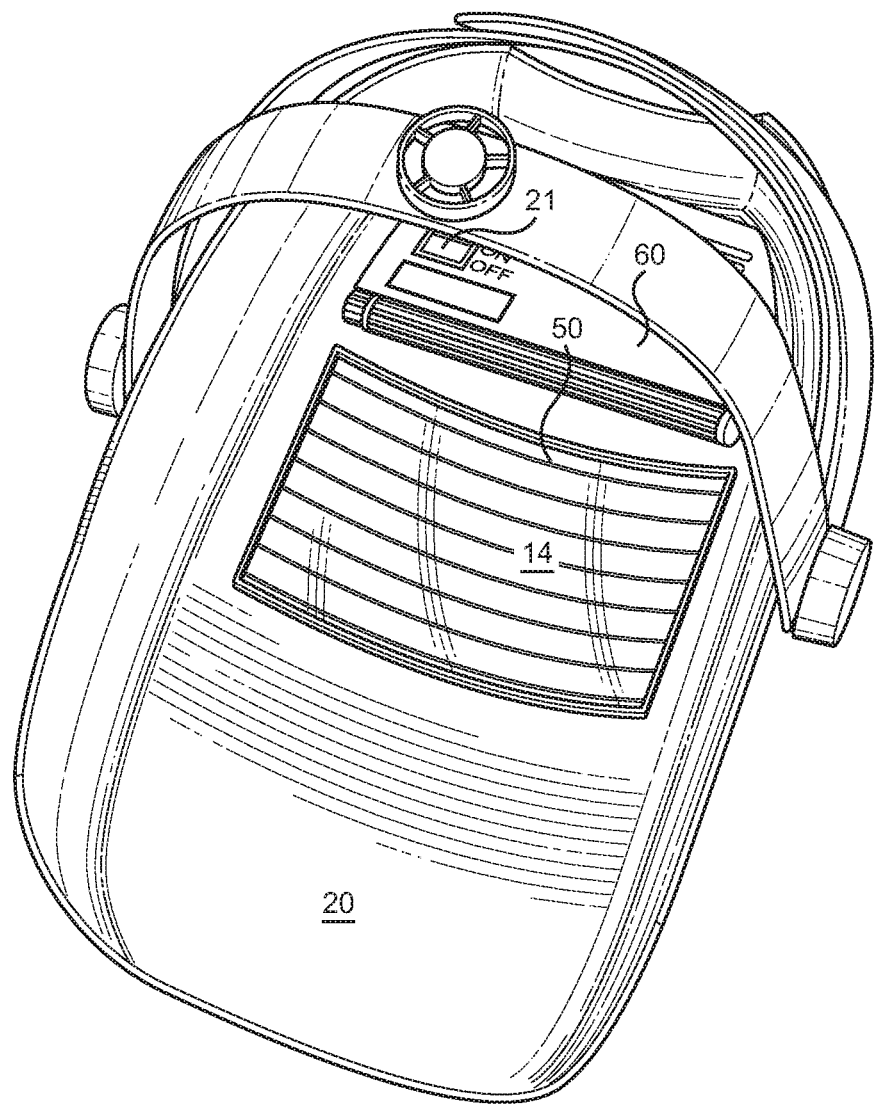
FIG. 5 shows yet another embodiment of the present invention, wherein a plurality of heating elements are disposed across the welding mask lens.

Referring now to FIG. 5, there is shown yet another feature of the present invention, wherein the lens 14 of the exemplary embodiment is provided an internal heating element 50 therein to assist in fog and condensation removal. In conjunction with the internal housing 60 that provides a current of heated air, a resistive heating element 50 imbedded within the lens 14 of the mask is contemplated. In this way, the user can request the heating element 50 function by way of the control switch 21, whereby the lens 14 is heated and fog is removed therefrom. Condensation and cold air is treated within the mask interior 20 by way of the forced air, while the direct application of heat within the lens 14 rapidly removes fog, as is experienced in vehicle windows.

When welding in cool, humid weather, near coastal regions or during the winter, the lens of a welding mask often becomes fogged. When this happens, a welder cannot see clearly and is forced to stop working to clear the lens for safety. The fogged lens could also create a safety hazard if a user is blindly welding, grinding, or buffing a work piece. Further still, the welder's finished product may be of lower quality if he or she cannot see properly. A solution is needed to allow welders to see clearly in any weather condition and any time of year.

The present invention relates to a welding mask having a forced air means and a heating means. More particularly, the present invention pertains to a defogging, anti-condensation, and anti-frost welding mask. The device comprises a fan and heating element that are installed inside a welding helmet, or alternatively the device comprises an accessory module that can be applied to traditional welding masks to accomplish the same purpose. The airflow keeps the lens of the welding mask clear and prevents condensation from building up, which improves visibility. This device can be used by any welder experiencing the effect of a fogged lens hindering his or her ability to see clearly while working in cold climates.

It is submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A cold climate welding mask, comprising:
    a mask structure having a mask wall, a mask interior, a mask headband, and a welding lens;
    a housing within said mask interior;
    said housing having an air intake, an exhaust port, a forced air mechanism and a heating mechanism within said housing;
    an electrical power source powering said forced air mechanism and said heating mechanism;
    a switch for operating said forced air mechanism and said heating mechanism;
    said switch comprising a first operating position, a second operating position, and a third operating position, wherein said first operating position is configured to activate only said forced air mechanism, said second operating position is configured to activate both said forced air mechanism and said heating mechanism, and said third operating position is configured to cease activation of both said forced air mechanism and said heating mechanism;
    said forced air mechanism drawing air into said housing interior over said heating mechanism and out of said exhaust port;
    said heating mechanism comprising a resistive heating element, said resistive heating element configured to operably heat said air; and
    said exhaust port comprising a vent configured to direct said air in a particular direction, said vent comprising a hand control thereon.

2. The device of claim 1, wherein said air intake further comprises an air filter element.

3. The device of claim 1, wherein said mask welding lens further comprises a lens resistive heating element therein.

4. The device of claim 1, wherein said forced air mechanism comprises an electrical fan.

5. The device of claim 1, wherein said electrical power source is a battery power supply within said housing.

6. The device of claim 1, wherein said electrical power source is a battery power supply connected by way of an electrical cord to an external battery pack.

7. The device of claim 1, wherein said electrical power source is a battery power supply connected to a photovoltaic cell.

8. A welding mask accessory assembly for use in cold climates, comprising:
    a housing having an interior cavity, an intake port, and an exhaust port;
    said housing having a forced air mechanism and a heating mechanism therein;
    an electrical power source powering said forced air mechanism and said heating mechanism;
    a switch for operating said forced air mechanism and said heating mechanism;
    said forced air mechanism drawing air into said housing interior and forcing said air over said heating mechanism and out of said exhaust port;
    said switch comprising a first operating position, a second operating position, and a third operating position, wherein said first operating position is configured to activate only said forced air mechanism, said second operating position is configured to activate both said forced air mechanism and said heating mechanism, and said third operating position is configured to cease activation of both said forced air mechanism and said heating mechanism;
    said heating mechanism comprising a resistive heating element, said resistive heating element configured to operably heat said air;
    said housing adapted to be attached to an interior surface of a welding mask;
    said exhaust port comprising a vent, wherein an angle at which the vent is positioned is adjustable via a control; and
    wherein said air is directable toward either one of said interior surface of said welding mask or lens of said welding mask.

9. The device of claim 8, wherein said air intake further comprises an air filter element.

10. The device of claim 8, wherein said forced air mechanism comprises an electrical fan.

11. The device of claim 8, wherein said electrical power source is a battery power supply along said housing.

12. The device of claim 8, wherein said electrical power source is a battery power supply connected by way of an electrical cord to an external battery pack.

13. The device of claim 8, wherein said electrical power source is a battery power supply connected to a photovoltaic cell.

* * * * *